United States Patent [19]
Kiri

[11] Patent Number: 4,761,802
[45] Date of Patent: Aug. 2, 1988

[54] HIGH-CONTRAST X-RAY IMAGE DETECTING APPARATUS

[75] Inventor: Motosada Kiri, Kyoto, Japan

[73] Assignee: Shimadzu Corporation, Kyoto, Japan

[21] Appl. No.: 916,617

[22] Filed: Oct. 8, 1986

[51] Int. Cl.$^4$ .................... G01N 23/00; H05G 1/64
[52] U.S. Cl. .................................. 378/99; 378/146; 378/147
[58] Field of Search ............... 378/99, 146, 147, 148, 378/149, 150, 152, 154; 358/111

[56] References Cited

U.S. PATENT DOCUMENTS

| | | | |
|---|---|---|---|
| 4,096,391 | 6/1978 | Barnes | 378/146 |
| 4,383,327 | 5/1983 | Kruger | 378/99 |
| 4,433,427 | 2/1984 | Barnea | 378/146 |
| 4,493,098 | 1/1985 | Riihimäki et al. | 378/146 |

FOREIGN PATENT DOCUMENTS 2452166  5/1976  Fed. Rep. of Germany ........ 378/99
0067847  4/1982  Japan .................................. 378/149

Primary Examiner—Carolyn E. Fields
Assistant Examiner—Joseph A. Hynds
Attorney, Agent, or Firm—Koda and Androlia

[57] ABSTRACT

An X-ray image detecting apparatus devised so as to project an X-ray image of an object on a image receiving plane made of two-dimensionally arrayed picture elements with the object irradiated by many thin scanning X-ray beams. The beams, which penetrate the object, scan coincidentally a limited number of the picture elements of which they take a charge respectively, causing the time of scanning the whole area of the image receiving plane to be short. The image signals successively outputted from the picture elements are stored in a memory with only their respective maximum values selected. Thus, the image signals are made free from being adversely affected by the stray X-rays scattered from the inside of the object, and provide a high-contrast X-ray image.

5 Claims, 3 Drawing Sheets

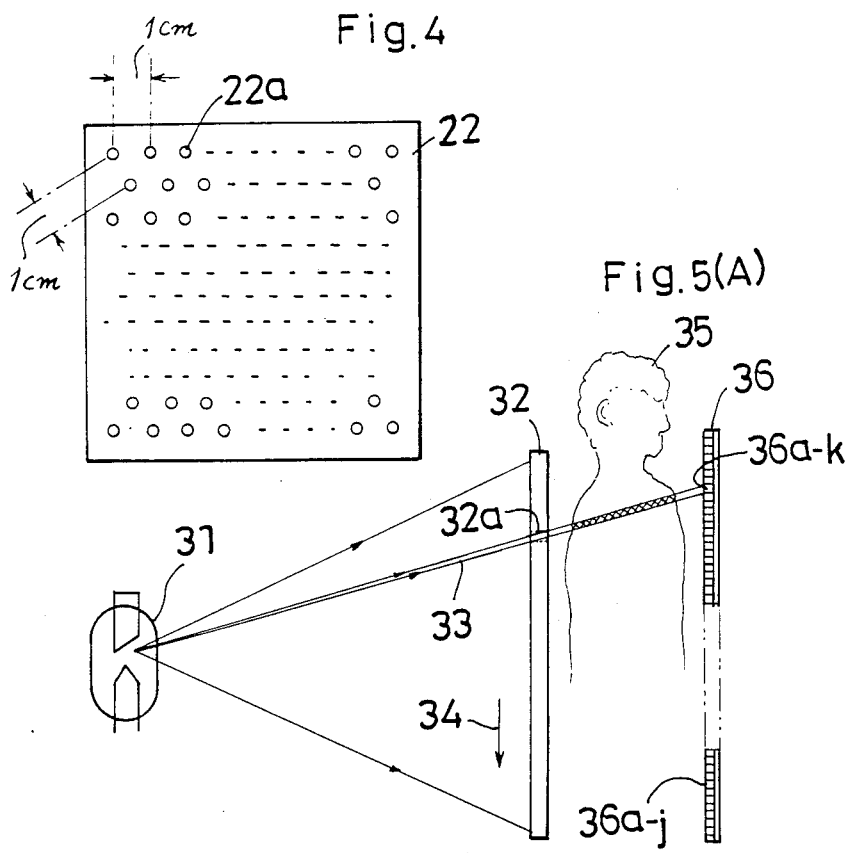
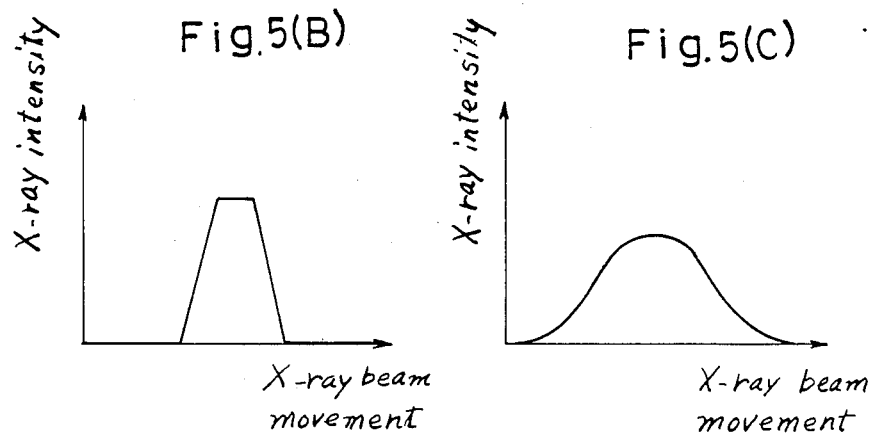

HIGH-CONTRAST X-RAY IMAGE DETECTING APPARATUS

BACKGROUND OF THE INVENTION

The present invention relates to an X-ray image detecting apparatus, and more particularly to an X-ray image detecting apparatus improved so as to provide a high-contrast X-ray image without taking a long time.

An X-ray image obtained by making X-rays penetrate the object with the rays given a conical expanse covering a predetermined entire area to be imaged, has its image contrast deteriorated under the influence of stray X-rays scattered from various portions within the object. A conventional way to avoid the contrast deterioration due to such stray X-rays is to complete an X-ray image by scanning an object onedimensionally with a thin flat X-ray beam diverging in the form of a fan, or preferably two-dimensionally with a thin linear X-ray beam, instead of radiating the object with a conically diverging flux of X-rays covering the entire expanse of the image. The stray X-rays can be decreased by decreasing the diverging solid angle of X-rays to be irradiated to the object. The decreased but still existing stray X-rays are prevented, for instance in case of the linear X-ray beam, with a pin-holed plate inserted between the object and an X-ray image receiving plane so as to make only the X-ray beam pass the pin hole provided to the above plate. However, such a conventional way is accompanied by an important disadvantage that it takes a long time to obtain a complete image owing to the period of time necessary for the scanning operation of the X-ray beam. In addition it is troublesome to make the pin-holed plate interlocked to the scanning movement of the X-ray beam.

OBJECTS AND SUMMARY OF THE INVENTION

The present invention aims at eliminating such a disadvantage accompanying the conventional way of avoiding the image contrast decrease due to stray X-rays, and makes it an object of the present invention to provide an X-ray image detecting apparatus improved so that a high-contrast X-ray image may be obtained in a short time without being adversely affected by the stray X-rays.

Another object of the present invention is to constitute such an improved apparatus in a simple construction.

To achieve the above objects, an apparatus according to the present invention comprises an ordinary X-ray source, a collimator plate provided with a two-dimensional array of small through holes, an X-ray image receiving means devised so as to output the image signal of a projected X-ray image in the form of a series of electric picture-element signals, and a memory for storing the picture element signals outputted from the X-ray image receiving means. The collimator plate is located between the X-ray source and an object whose inner structure is to be imaged.

BRIEF DESCRIPTION OF THE DRAWINGS

The details of the present invention are described in the following on reference to the accompanying drawings, in which:

FIG. 4 shows a front view of another collimator plate usable in the present invention;

FIG. 5(A) is a schema of the spot X-ray image projecting system on which the principle of the present invention is based; and FIG. 5(B) and 5(C) respectively show an ideal and a practical X-ray intensity variations on a unit X-ray detector in the X-ray receiving plane of the above system shown in FIG. 5(A).

DETAILED DESCRIPTION OF THE INVENTION

Figure 1A:
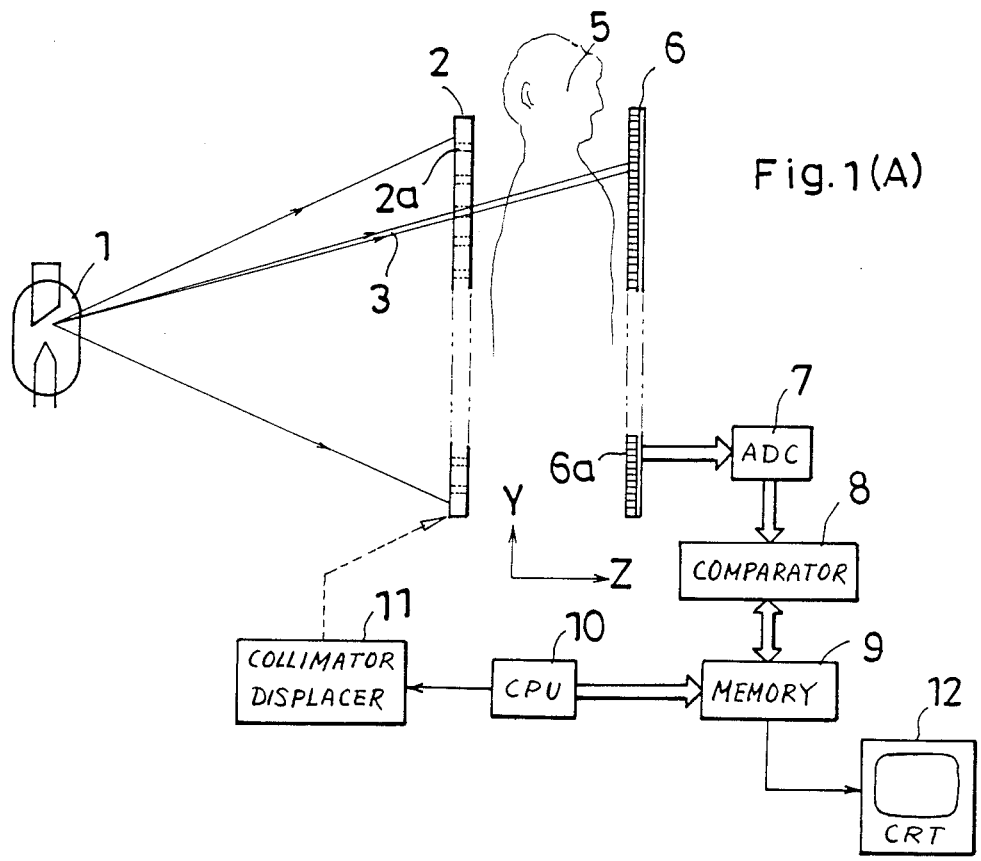
FIG. 1(A) is a schema representing the constitution of an embodiment of the present invention.

Referring to FIG. 5(A), which is one of the drawings illustrating the principle of the present invention, X-rays radiated from an X-ray source 31 are collimated to a thin X-ray beam 33 by a collimator plate 32 having a through hole 32a and made to penetrate an object 35, projecting a spot X-ray image on an X-ray image receiving plane 36 made up of two-dimensionally arrayed unit X-ray detectors $36a$-$j$ ($j=1,2,\ldots$), by which the plane 36 is divided into picture elements. In such a spot X-ray image forming system, as the collimator plate 32 is moved in parallel to the X-ray image receiving plane 36, for example, vertically as indicated with an arrow 34, the spot X-ray image made by the beam 33 moves on the plane 36 downward, sweeping a representative unit X-ray detector $36a$-$k$. Then the detector $36a$-$k$ should ideally output a picture-element signal as angular as shown in FIG. 5(B). However, a real output of the detector is rounded as shown in FIG. 5(C) owing to the influence of not completely ignorable stray X-rays scattered from the region through which the thin X-ray beams 33 passes. Anyway, the peak value of the intensity variation at the unit X-ray detector $16a$-$k$ may well be employed as the spot image representing a double-hatched portion of the object 35. Therefore, if the collimator plate 32 is moved two-dimensionally in such a wide range as to make the beam 33 scan an entire region to be imaged, the various portions included in the region are successively spot-imaged on the unit X-ray detectors $16a$-$j$ constituting the picture elements. All the (electric) spot image signals outputted from the unit X-ray detectors $16a$-$j$ are stored as picture element signals at their respective addresses provided in a memory (not shown). The picture element signals stored in the memory is used to display on a CRT the entire picture of the detected X-ray image. According to the above method as it is, however, it takes a long time to complete one X-ray image because the entire region to be detected is scanned with one X-ray beam 33. Therefore, the present invention employs a multi-through hole collimator plate provided with a plurality of two-dimensionally arrayed through holes. With this constitution of the collimator plate, the range of the collimator plate movement can be restricted to half the arrangement pitch of the through holes because the scanning of the unit detectors $16a$-$j$ constituting the X-ray receiving plane 6 is shared by a plurality of thin X-ray beams made by the above described two-dimensionally arrayed through holes.

Figure 1B:
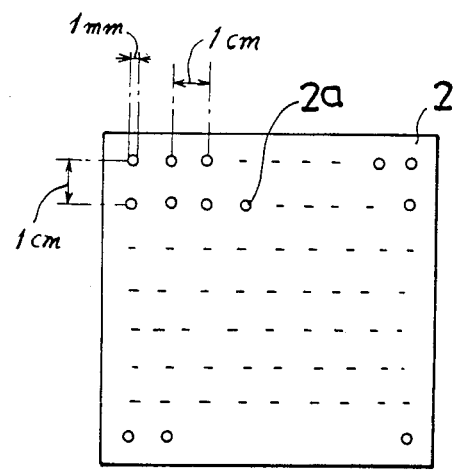
FIG. 1(B) shows the front view of a collimator plate used in the present invention.

Referring to FIG. 1(A), which shows a schema of an embodiment of the present invention, the apparatus consists of an X-ray source 1, a collimator plate 2 having a plurality of two-dimensionally arrayed through holes (collimating holes) 2a, an X-ray image receiving plane 6 consisting of a two-dimensional array of unit X-ray detectors 6a, an A-D converter 7, a comparator 8, a memory 9, a CPU 10, a collimator displacing mechanism 11 and a RT 12. The collimator plate 2 is made of an X-ray stopping material such as a lead plate reinforced mechanically on both sides with ordinary metal plates, and the collimating holes 2a provided thereon have a diameter of about 1 mm and an arrangement pitch of about 1 cm, as is illustrated in FIG. 1(B). The collimator plate displacing mechanism 11, which is operated by the instruction of the CPU 10, moves the collimator plate 2 two-dimensionally in parallel to the X-ray receiving plane 6 in a range equal to the arrangement pitch of the collimating holes 2a.

In such a constitution of the apparatus, the collimator plate 2 makes a plurality of thin X-ray beams 3 (only one representative beam is drawn) corresponding to the number of collimating holes 2a. The thin beams 3 project their respective spot X-ray images on the X-ray image receiving plane 6, making the unit X-ray detectors 6a successively output their respective image signals in time-series in accordance with the movement of the collimator plate 2, each of which image-signals shows a time-variation similar to that illustrated in FIG. 5(C). The image signals outputted from the unit X-ray detectors 6a are sampled and converted to digital signals by the A-D converter 7 and then compared by the comparator 8 with the image signals previously stored in the corrresponding addresses in the memory 9. In the course of signal comparison, if and only if the signals newly outputted from the unit X-ray detectors 6a are larger than those stored previously in the memory 9 are replaced with the new signals with respect to every address in the memory 9. Thus, after the beams 3 have scanned all the unit X-ray detectors of which they have a charge, all of the addresses in the memory 9 store the peak values of the spot X-ray image signals outputted from the corresponding unit X-ray detectors 6a. Then, the contents stored in the memory 9 are read out and used to display on the CRT 12 an entire X-ray picture of the portion penetrated by the scanning X-ray beams 3 irradiated to the object 5. The operation of the apparatus is controlled by the CPU 10.

Figure 2:
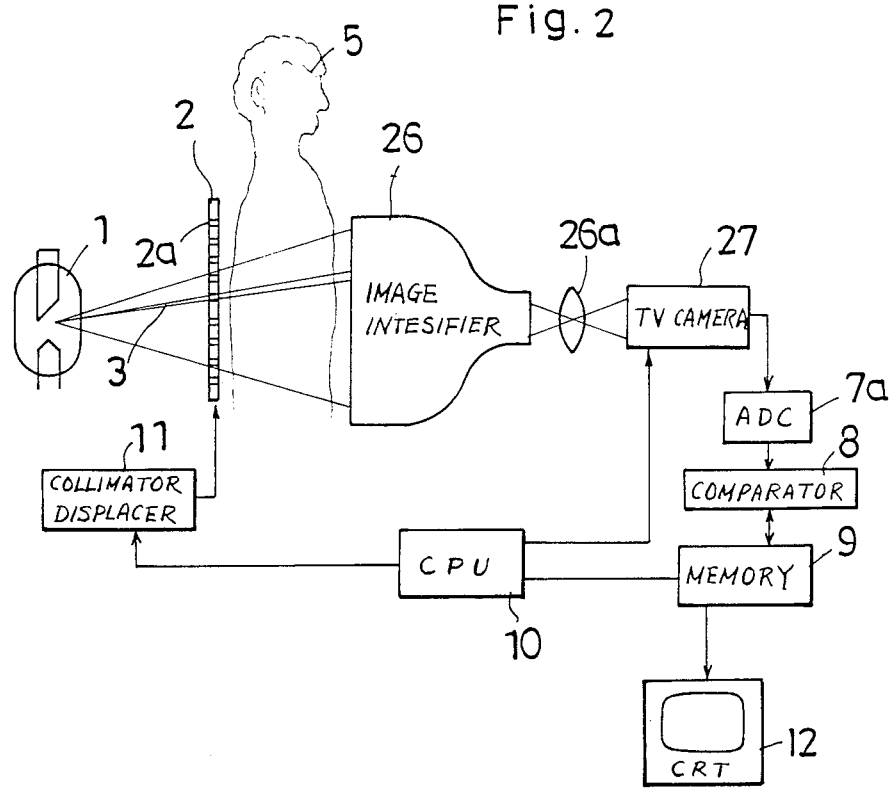
FIG. 2 is a schema representing the constitution of another embodiment of the present invention.
Figure 3:
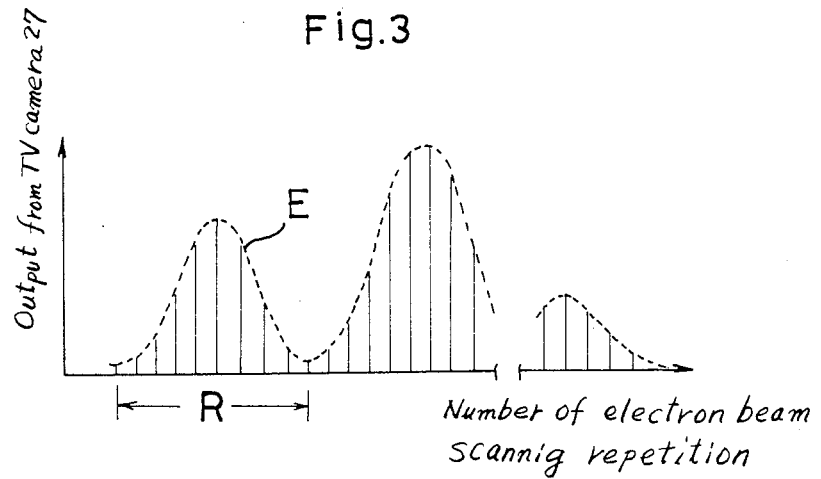
FIG. 3 shows the X-ray image signals in the embodiment shown in FIG. 2.

The present invention can further be embodied as follows. Referring to FIG. 2, which is a schema representing the constitution of another embodiment of the present invention, the same constituent elements in FIG. 2 as those used in FIG. 1(A) are indicated with the same reference signs. In this embodiment, the X-ray image receiving plane 6 used in FIG. 1(A) is replaced by an X-ray image intensifier 26. The moving invisible spot X-ray images projected on the image intensifier 26 by the moving thin X-ray beams 3 (only one of which is drawn in FIG. 3) are visible-imaged and re-projected on a TV camera 27 through an optical system 26a (represented by only one lens). In this case the TV camera 27 has its electron scanning performed intermittently so as to make the scanning trace form virtual picture elements corresponding to the picture elements constituted, in FIG. 1(A), with X-ray detectors 6a. Considering that the electron scanning in the TV camera 27 is very much faster than the scanning of the X-ray beams 3, the TV camera 27 outputs such intermittent signals as shown in FIG. 3, in which the horizontal coordinate stands for the number of repetition of the electron scanning. Further, the intermittent signals in a region indicated by R belong to a specific one of the above mentioned virtual picture elements, and an envelope E indicated with a dotted line corresponds to the curve shown in FIG. 5(C). Because the intermittent signals outputted from the TV camera 27 correspond to the signals obtained, in the previous embodiment, by sampling the output from the unit X-ray detectors 6a by the A-D converter 7 in advance of being converted to digital signals by the same, an A-D converter 7a (in FIG. 2) in this embodiment only digitalizes the signals shown in FIG. 3, thereby outputting the X-ray image signals similar to those outputted from the A-D converter 7 in FIG. 1(A). The following sequence of image signal processing is the same as that in the preceding embodiment, and therefore, deleted.

Both the above described embodiments can be modified by using a collimator plate 22 as shown in FIG. 4, instead of the plate 2 shown in FIG. 1(B). In FIG. 4 the collimator plate 22 is provided with through holes 22a with their positions staggered. Besides, the number of holes is increased by about 1.7 ($=\sqrt{3}$) times the number in the case of the collimator plate shown in FIG. 1(B). Further, each of the unit X-ray detectors 6a (in FIGS. 1(A)) can be constituted either with a single element capable of converting X-rays to electric signals directly or with a combination of an X-ray scintillator and a photosensor coupled to the scintillator.

According to the present invention, as is understood from the above descriptions, a high-contrast X-ray image is easily detected in a relatively short time without being adversely affected by stray X-rays in substance, because the thin X-ray beams 3 decrease the size of the regions penetrated by the beams 3 and because the plurality of the scanning X-ray beams 3 makes the necessary region of X-ray beam scanning narrow.

I claim:
1. An X-ray image detecting apparatus comprising:
an X-ray source;
a collimator plate placed between said X-ray source and an object whose X-ray image is to be detected, said collimator plate being provided with two-dimensionally arrayed X-ray collimating through holes to make a plurality of thin X-ray beams from widely diversing X-rays from said X-ray source;
an X-ray image receiving means for converting an X-ray image projected thereon to an electric image signal, said X-ray image receiving means being devised so as to detect said X-ray image with the same divided into pixels so that said electric image signal may be outputted in the form of pixel signals from said X-ray image receiving means;
a collimator plate displacing means for moving said collimator plate two-dimensionally in parallel to said X-ray image receiving means so that the same may be scanned by said thin X-ray beams made by said X-ray collimating through holes provided in said collimator plate;
a memory means having addresses corresponding to said pixels for storing said electric image signal in the form of the pixel signals; and
a signal comparator means for comparing, with regard to each of said addresses of said memory, a previously sampled and stored value of a pixel signal with a succeedingly sampled value of the pixel signal and replacing the contents of each address with a succeedingly sampled pixel signal if the latter value is larger than the former one, such that each of the addresses in said memory may finally store the maximum value of a corresponding pixel signal which varies showing a peak in the process of the scanning of a corresponding X-ray beam made by said collimator plate.

2. An apparatus defined in claim 1, wherein said X-ray image receiving means is constituted with an X-ray image receiving plane made up of a two-dimensional array of pixel unit X-ray detectors.

3. An apparatus defined in claim 1, wherein said X-ray image receiving means consists of an assembly of an X-ray image intensifier and a TV camera optically coupled to said X-ray image intensifier, and wherein the electron beam scanning in said TV camera is performed not continuously, but intermittently to detect an X-ray image in the form of pixel signals.

4. An apparatus defined in claim 2, wherein said pixel unit X-ray detectors are elements capable of directly converting X-rays to electric signals.

5. An apparatus defined in claim 2, wherein each of said pixel unit X-ray detectors is a combination of an X-ray scintillator and a photosensor coupled to said X-ray scintillator.

* * * * *